(12) United States Patent
De Angelis et al.

(10) Patent No.: US 7,105,700 B2
(45) Date of Patent: Sep. 12, 2006

(54) PROCESS FOR THE SYNTHESIS OF MIXTURES OF METHANE DIPHENYL DIAMINE AND ITS HIGHER HOMOLOGUES WITH A CONTROLLED ISOMER DISTRIBUTION

(75) Inventors: Alberto De Angelis, Legnano (IT); Carlo Perego, Carnate (IT); Otello Farias, Rome (IT); Aldo Bosetti, Vercelli (IT)

(73) Assignee: Dow Global Technologies Inc., Midland, MI (US)

( * ) Notice: Subject to any disclaimer, the term of this patent is extended or adjusted under 35 U.S.C. 154(b) by 174 days.

(21) Appl. No.: 10/476,955

(22) PCT Filed: Apr. 29, 2002

(86) PCT No.: PCT/EP02/04714

§ 371 (c)(1),
(2), (4) Date: Apr. 29, 2004

(87) PCT Pub. No.: WO02/088067

PCT Pub. Date: Nov. 7, 2002

(65) Prior Publication Data

US 2004/0181092 A1    Sep. 16, 2004

(30) Foreign Application Priority Data

Apr. 27, 2001    (IT)    ............................... MI01A0880

(51) Int. Cl.
*C07C 209/54*    (2006.01)
(52) U.S. Cl. ........................................ 564/330; 564/332
(58) Field of Classification Search ..................... None
See application file for complete search history.

(56) References Cited

U.S. PATENT DOCUMENTS 5,756,802 A * 5/1998 Li et al. ..................... 558/319

OTHER PUBLICATIONS

Database CAPLUS on STN, Acc. No. 2001:17318, Li et al., Xinshiji De Cuihau Kexue Yu Jishu, Quanguo Cuihuaxue Jihuiyi Lunwenji, 10th, Zhangjiajie, China, Oct. 15-19, 2000, p. 57-58 (conference abstract).*
Database CAPLUS on STN, Acc. No. 2000:491525, Huang et al., Studies in Surface Science and Catalysis (2000), 129 (Nanoporous Materials II, Processing of the Conference on Access in Nanoporous Material, 2000), p. 93-98 (abstract).*
Database CAPLUS on STN, Acc. No. 1994:704443, Corma Canos et al., WO 9421378 (Sep. 29, 1994) (abstract).*
Database CAPLUS on STN, Acc. No. 1988:630193, Deng et al, Huaxue Xuebao (1988), 46(4), p. 321-326 (abstract).*
Database CAPLUS on STN, Acc. No. 1988:630406, Zhao, Yingyong Huaxue (1988), 5(3), 89-91 (abstract).*
Databaxe CAPLUS on STN, Acc. No. 1997:534806, Wang et al., Fujian Shifan Daxue Xuebao, Ziran Kexueban (1997), 13(1), p. 52-55 (abstract).*
Huang et al, Chemistry Letters (1999), 8, p. 829-830.*

* cited by examiner

*Primary Examiner*—Brian Davis

(57) ABSTRACT

A process for preparing methane diphenyl diamine (MDA) or a mixture of methane diphenyl diamine (MDA) and its higher homologues with a controlled isomer distribution using a modified zeolite having "shape selectivity". The mixture contains compounds having the following general formula (I): where R represents a hydrogen atom or a C1 to C8 (iso)alkyl group, a C4 to C10 cycloalkyl group or a C6 to C12 aromatic group and n is a whole number greater than or equal to one so as to give a functionality of 2 to 6.

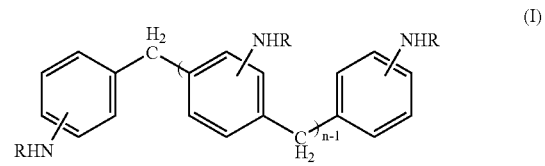

(I)

22 Claims, No Drawings

PROCESS FOR THE SYNTHESIS OF MIXTURES OF METHANE DIPHENYL DIAMINE AND ITS HIGHER HOMOLOGUES WITH A CONTROLLED ISOMER DISTRIBUTION

This invention relates to a process for preparing methane diphenyl diamine (MDA) or a mixture of methane diphenyl diamine (MDA) and its higher homologues with a controlled isomer distribution. More specifically, this invention relates to a process for the preparation of MDA or of mixtures of MDA and its higher homologues, in which the said mixture contains compounds having the following general formula (I):

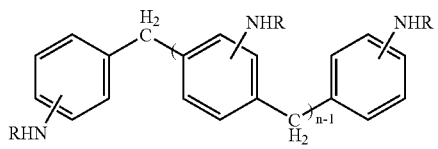

where R represents a hydrogen atom or a C1 to C8 (iso)alkyl group, a C4 to C10 cycloalkyl group or a C6 to C12 aromatic group and n is a whole number greater than or equal to one so as to give a functionality of 2 to 6, in which it is possible to control the concentration of dimeric products, in particular of isomer 4.4'-MDA with respect to isomers 2.4'-MDA and 2.2'-MDA.

Methane diphenyl diamine or the methane diphenyl diamine mixtures are used as intermediates in the preparation of the corresponding methane diphenyl diisocyanate (MDI), in turn used in the synthesis of a series of polymers for example polyurethanes, thermoplastic polymers and epoxy resins.

Methane diphenyl diamine may be produced from aniline or from one of its derivatives by condensation with formaldehyde in the presence of solutions of strong acids, such as hydrochloric acid, sulphuric acid and phosphoric acid, as described, for example, in U.S. Pat. Nos. 2,683,730, 3,277,173, 3,344,162; 3,362,979 or in H. Ulrich, "Chemistry and Technology of Isocyanates" John Wiley and Sons, USA, 1996. The operating conditions, necessary to produce a product with the specific structural characteristics and without the formation of undesirable amounts of by-products, typically requires the use of a sizable quantity of strong acid and consequently the use of large quantities of materials in the equipment which are capable of resisting such acids. Such construction materials are often expensive. Further, after the MDA has been synthesised, a corresponding amount of base material (typically sodium hydroxide) is needed to neutralise the acid used, leading to the formation of sizable quantities of salts which may be contaminated by aromatic products and which need to be discharged. All these requirements result in an increase in production costs.

Production processes based on using strong acid catalysts in which, for example the synthesis is carried out in the presence of hydrophobic solvents in order to totally or partially recycle the acid catalyst in an aqueous stage are known. These types of procedures introduce a solvent, which may be chlorinated and thus environmentally disadvantageous, to the process and are described, for example, in U.S. Pat. No. 4,924,028 and U.S. Pat. No. 4,914,236.

To improve the process the use of other solvents (generally chlorinated) different from the initial substrate has been contemplated. However chlorinated solvents may increase the risk of environmental damage.

U.S. Pat. No. 4,039,580 and U.S. Pat. No. 4,039,581 describe the use of reusable solid acids, in particular clays, in the synthesis of MDA from aniline and formaldehyde. In particular, the process in U.S. Pat. No. 4,039,581 allows for the low temperature pre-condensation between aniline and formaldehyde and the elimination of water and methanol. Aminals are also obtained which come into contact with the solid acid catalyst, at a temperature of between 20 and 55° C. to produce the corresponding benzylamines. The benzylamines is then converted to the end products.

U.S. Pat. No. 4,071,558 describes a process using a solid acid catalyst for example Superfiltrol, in which the distribution of the dimeric products is modulated, in particular of isomer 2.4'-MDA, based on selecting the operating conditions of condensation.

These are disadvantageous in that the acid catalysts generally require very low levels and suitably an absence of water in the aniline acetal. The water content is suitably not greater than 3% in weight, and preferably less than 0.15% in weight, in order to avoid deactivation of the catalyst. Clays also present problems because they may be reused a limited number of times and, since their origin is natural and not synthetic, consistent performance cannot be entirely reproduced depends on the particular batch.

The Applicants have now found a procedure for the preparation of MDA in a mixture with its higher homologues which allows distribution between the main dimeric products to vary over a wide range and reduce or avoid disadvantages with known processes. The ability to control the variation in the distribution allows a range of derivative products to be obtained such as isocyanates, for example obtained by the phosgenation of MDA, with characteristic features. Further, the resulting MDA mixture is particularly advantageous because MDA isomers are typically very difficult to separate from each other. U.S. Pat. No. 4,034,039 discloses a process in which separation of MDA isomers takes place through successive fractionated crystallization of MDA and phenol mixtures. To be able to control the isomer distribution enables a spectrum of products having clearly different characteristics to be obtained allowing products to be tailored for use in a variety of market applications.

The present invention is based on the surface modification of a zeolite catalyst in acid form, described below, with an aqueous acidic solution comprising phosphoric acid and/or boric acid, "as is", and, optionally, comprising a salt, for example an ammonium salt, thereof suitably, after treatment with an aqueous wash, solvent is removed and the catalyst calcined.

Without wishing to be bound by any theory, it is believed that phosphoric acid and/or boric acid and the, if present their salts combine with the zeolite's surface and, following a thermal treatment step give rise to species, believed to be polymer compounds which modify pore size and shape characteristics. "Catalysis on ZSM-5 zeolites modified by phosphorus" G. Oehlmann et al, Studies in Surface Science and Catalysis. Vol. 65, (1991), pages 1–20 illustrates methods by which pore size and shape of zeolites may be modified.

Modifying the pore size and shape in a zeolite catalyst provides a means of influencing catalyst selectivity ("shape selecting").

Surprisingly, it was found that "shape selectivity" effects the ratios of MDA isomeric distribution synthesized by means of acid catalysis, especially favouring the 4.4'-MDA isomer among the dimer products. Such variation of the isomer distribution may be modified and controlled by changing the process with which phosphoric acid or boric acid is combined with the zeolite. Furthermore, it has been found that zeolite in powder form and zeolite already in extruded form in the presence of a binder, for example, boehmite may be treated advantageously to provide "shape selecting".

This invention provides a process for the preparation of MDA or a mixture of MDA and its higher homologues having the general formula (I):

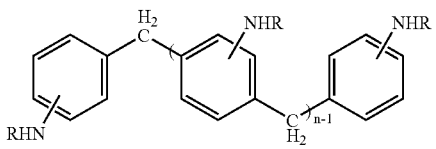

where R is independently selected from hydrogen, a C1 to C8 alkyl group, a C4 to C10 cycloalkyl group and a C6 to C12 aromatic group and n is a whole number greater than, or equal to one, suitably from 1 to 5 so as to give a functionality from 2 and 6, which comprises carrying out the re-arrangement reaction of the intermediate having general formula (II):

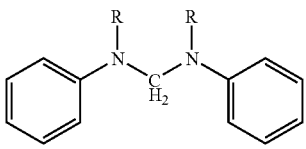

in the presence of a zeolite in acid form with a "spaciousness index" from 2.5 to 19 modified on the surface by a process comprising i) one or more treatments, for example impregnations, with an aqueous solution comprising phosphoric acid and/or boric acid, as is, and, optionally, comprising a salt, for example an ammonium salt thereof, ii) removal of at least part of the solvent and iii) calcining the treated catalyst, preferably at a temperature of at least 400° and especially at least 500° C.

Reference to "alkyl" herein shall be taken to include linear alkyl and branched or "iso" alkyl groups unless otherwise stated.

The "spaciousness index" parameter measures the effective pore diameter of porous materials, such as zeolites. The "spaciousness index" is a parameter described in literature as, for example, in U.S. Pat. No. 4,795,847 and in "Zeolites and Related Microporous Material: State of the Art 1994", Studies in Surface Science and Catalysis, vol. 84, 37, 1994, Elsevier Science B. V.; "Zeolite: Facts, Figures, Future", 1989, 1115, Elsevier Science Publishers, B. V.

According to the present invention, zeolites with a preferred "spaciousness index" of between 2.5 and 19 suitably are crystalline material having the composition (III):

$$M^{n+}{}_{x/n}[(AlO_2)^-{}_x(SiO_2)].(H_2O)_p \qquad [III]$$

where x is less than 1, p is a whole number greater than or equal to 1, preferably from 1 to 20, M is a metal from Group IA or IIA, or is a lanthanide, n is the valency of M, and where M may be partially or totally exchanged for $H^+$, $(NH_4)^+$, or $(NR'_4)^+$ where R' is an alkyl group, for example C1 to C4 alkyl, or an aryl group.

Examples of zeolites which fall under the general formula (III) and which have a "spaciousness index" from 2.5 to 19 include beta zeolite, mordenite, ZSM-12, MCM-22 and ERB-1. Particular preference is given to beta zeolite, for example as described in U.S. Pat. No. 3,308,069 with a "spaciousness index" of 19 and to zeolite ZSM-12.

Suitably the treatment of the zeolite is carried out by impregnation, in particular by submerging solid particles of the zeolite in a liquid phase comprising phosphoric acid and/or boric acid, as is acid, as is, and, optionally, comprising a salt, for example an ammonium salt thereof, diluted in water at a concentration from 0.1 and 10% by weight. Suitably the treatment is carried out at a temperature of 20 to 100° C. At the end of this treatment, the liquid phase is removed, at least in part, from the solid desirably by distillation under a vacuum. Suitably the remaining solid is calcined, preferably at a temperature of 500 to 600° C. The treatment may be repeated two or more times, for example 3 to 5 times, with each treatment being followed by the corresponding removal of liquid and calcination stage. The acid and optionally salt may be the same or different in each treatment.

The zeolite used to prepare the catalyst employed in the present invention is suitably in acid form, that is, in the form in which hydrogen ions occupy most of the cationic locations. In the surface modification treatment the zeolite may be used "as is" or may be modified before the treatment by the partial isomorphic substitution of aluminium by a metal selected from boron, iron and gallium. At the end of the treatment, the catalyst may be used "as is" or in combination with a binder, for example boehmite and alumina. The catalyst may be shaped in extruded tablets, for example as described in EP-A-847,802, or in any other suitable form. The surface tretment may be carried out on extruded tablets of the untreated zeolite if desired.

Suitably, the rearrangement reaction is carried out at a temperature of 50 to 250° C., preferably from 120 to 200° C., in the presence of a solvent. Examples of suitable solvents include optionally substituted aliphatic hydrocarbons, optionally substituted aromatic hydrocarbons, halogenated aromatic hydrocarbons and aniline. Examples of solvents which are particularly suitable are aniline and aromatic chlorinated hydrocarbons such as m-dichlorobenzene and chlorobenzene.

The intermediate in general formula (II) is a product referred to in the literature, in particular when R is hydrogen. This intermediate may be obtained by condensing aniline, or derived from aniline in which R is different from hydrogen, with formaldehyde, or a compound capable of producing formaldehyde under reaction conditions. In particular, formaldehyde may be used in an aqueous solution such as formaldehyde in an oligomerous state (for example trioxane and paraformaldehyde), dissolved in a solvent, suitably with aniline/formaldehyde molar ratios of 2 to 10, preferably from 3 to 5. At the end of the synthesis, the intermediate in formula (II) is desirably separated by known methods, for example physical separation and distillation. The product thus obtained may contain water but the water content suitably is 3% or less by weight and preferably 1.5% or less.

In a further aspect, the invention provides a process for the preparation of methane diphenyl diamine in general formula (I) in which the rearrangement reaction may be carried out by contacting the zeolite catalyst with a reaction mixture comprising aniline, or a derivative of aniline, and formaldehyde, or a compound capable of producing formaldehyde under the reaction conditions. In this case, the aniline, or its derivative, is preferably present in stoichiometric excess and may act as both a reagent and a solvent for the reaction at the same time.

The rearrangement reaction may be carried out discontinuously, continuously or semi-continuously at ambient pressure or elevated pressure such as to maintain the reactive system in a liquid state.

In a preferred embodiment, a procedure for the production of a compound having general formula (I) comprises:
(a) reacting aniline, or a derivative of aniline and formaldehyde, or a precursor of formaldehyde, so as to form an amine of formula (II) optionally in a solvent, preferably aniline or its derivative in the event that the aniline or its derivative is used in sufficient excess;
(b) removing water if present, from the amine (II) to a residual concentration
of water of 3% or less, for example 1 to 3%, by weight of the amine (II);
(c) optionally diluting the product of step (b) in a solvent;
(d) isomerising the amine (II) by feeding it into a reaction zone, preferably one or more fixed bed reactors, containing a zeolite in acid form with a "spaciousness index" of 2.5 to 19, modified on the surface by a process comprising i) one or more treatments, for example impregnations, with an aqueous solution comprising phosphoric acid and/or boric acid, as is, and, optionally, comprising a salt, for example an ammonium salt thereof, ii) removal of at least part of the solvent and iii) calcining the treated catalyst, preferably at a temperature of at least 400° and especially at least 500° C., and wherein the reaction zone in step d) is at an ambient pressure or such as to maintain the reagent mixture in a liquid state and, preferably at a temperature of 50 to 250° C., more preferably 120 to 200° C.;
(e) recovering the methane diphenyl diamine, and/or its higher homologues, preferably by a purification process, for example, distillation.

According to the present invention, the reagents in step (a) may be fed discontinuously, continuously or semi-continuously to the reaction zone, suitably beginning with aniline and formaldehyde (or their derivatives or precursors). The pre-condensed material is subsequently fed into the reaction zone, preferably a fixed bed reactor, containing the treated solid acid catalyst, after water has been removed.

In step a), the reactants suitably are used in proportions from between 2 to 15 moles of aniline or a derivative of it per mole of formaldehyde. Preferably the reaction in step (a) is carried out at a temperature of between 10 to 60° C. and in the absence of an acid catalyst.

The pre-condensed amine (II) may be fed to the reaction zone by staggering by using a vertical reactor fitted with two or more lateral inlets in a so-called split-feed.

Suitably, the separation of water from the amine (II) is carried out in accordance with conventional techniques for example decanting and distillation. The separation may be carried out at variable temperatures or pressures according to the degree of residual water which it is desired to have in the amine solution (II). Separating the water may also be carried out by using a combination of the techniques referred to, such as, for example, decanting followed by distillation.

At the end of the rearrangement reaction of the amine (II), the distribution of the components in the composition of the mixture obtained after isomerisation may subsequently be modified by totally or partially recycling the mixture itself in the amine (II) synthesis reaction zone in step a) and/or in the rearrangement or isomerisation reaction zone.

A further process for the production of a compound having general formula (I) comprises reacting aniline, or one of its derivatives, and formaldehyde, or one of its precursors, in one single reaction step, preferably in a complete mixing reactor, in the presence of a zeolite in acid form with a "spaciousness index" of 2.5 to 19 modified on the surface by a process comprising i) one or more treatments, for example impregnations, with an aqueous solution comprising phosphoric acid and/or boric acid, as is, and, optionally, comprising a salt, for example an ammonium salt thereof, ii) removal of at least part of the solvent and iii) calcining the treated catalyst, preferably at a temperature of at least 400° and especially at least 500° C., and removing, preferably continually, for example by distilling, the water of reaction or additional water with one or more reagents.

Suitably, the order of the single stage process is based on the use of slurry reactors, either shaken or bubbled. Both the reagents, aniline (or one of its derivatives), and formaldehyde, (or one of its precursors), and the solid acid catalyst, optionally in the presence of a solvent which preferably comprises excess aniline or its derivative are fed, preferably simultaneously into a slurry reactor. Feeding of the reagents may be carried out continuously or by staggering the addition along with one or more components of the reaction mixture.

The aniline/formaldehyde molar ratio used suitably is from 2 to 15, and preferably from 3 to 5. Suitably the reaction temperature is from 50 to 250° C. and preferably from 120 to 200° C. Suitably, the pressure is that generated by the water with the reagents, or that which is generated during the reaction. Preferably the reaction mixture is continually agitated by an appropriate distillation system fitted to the reactor. The residence times in the liquid stage are suitably from 0.5 to 10 hours and preferably from 1 to 8 hours.

In the event the catalyst is to be replaced, the catalyst suitably is totally replaced within a period of 5 hours to a period of 30 hours. Preferably, the catalyst/load weight ratio is between 1/20 and 1/300.

At the end of reaction, the catalyst suitably is filtered, and any excess aniline (and any residual water and/or solvent which may remain) are removed from the required product by conventional techniques, for example by distillation.

The mixture of methane diphenyl diamine and/or its higher homologues synthesised in accordance with the process described above may be converted into the corresponding mixture of isocyanates in accordance with the techniques referred to.

In order to understand the present invention better and to put it into practice, there follow some examples which are for the purposes of illustration and are not exhaustive.

EXAMPLE 1

Amine Synthesis (Reaction Intermediate)

The reaction intermediate in the formula:

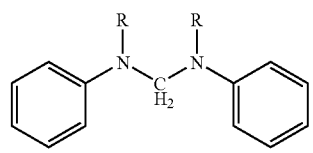

is prepared by condensation between aniline and formaldehyde. In particular, an aqueous solution with 37% formaldehyde is fed, while being stirred, into a reaction vessel containing aniline in order to have a formaldehyde/aniline molar ratio equal to four: the temperature is slowly raised to 50° C.

When the solution has been added, it is continued to be stirred for one hour, and then the organic stage consisting of amine and the aniline which has not reacted are then separated by a separator funnel. The organic stage is then dried to a maximum water content of 1.25% and retained for later use.

EXAMPLE 2

Zeolite Beta Synthesis 58.8 g of tetraethyl ammonium hydroxide in aqueous solution 40% by weight and 1.9 g of sodium aluminate (56% of $Al_2O_3$) are added to 58.4 g of demineralized water. It is heated to approximately 80° C. and it is left under agitation until completely dissolved.

The clear solution thus obtained is added to 37.5 g of LUDOX HS colloidal silica with 40% by weight of $SiO_2$. An homogeneous solution is obtained, with a pH of 14, which is poured into a steel autoclave and left to crystallize under hydrothermal conditions of 150° C. for 10 days, under static conditions and autogenous pressure.

The crystallized product is separated by filtration, re-dispersed in demineralized water and filtered again. A damp zeolite cake is obtained which contains the organic template tetraethylammonium and sodium.

EXAMPLE 3

Zeolite Beta Synthesis

The damp zeolite slab, prepared as described above in example 2 is dried in a oven for 1 hour at 150° C., calcined in a chamber furnace for 5 hours at 550° C. in an air stream.

The calcined solids are dispersed in an aqueous solution of ammonium acetate (150 g water and 8 g ammonium acetate) for the ion exchange. This suspension is heated under agitation for one hour approximately at 80° C.

The suspension is then filtered and the obtained solids are re-dispersed in demineralized water (150 ml) to be washed. The suspension is then filtered and the ion exchange and the previous washing are repeated in sequence. The solids are then washed again and dried in a oven for one hour at 150° C. thus obtaining zeolite in ammonic form. Said zeolite is calcined in a chamber furnace for 5 hours at 550° C. in an air stream, obtaining zeolite beta (spaciousness index=19) in acid form.

An elementary chemical analysis shows the sodium residue in this zeolite to be 106 ppm whereas the aluminum content is 3.14% ([Al]/[Na]=252).

The product is characterized through X ray diffraction from powders.

EXAMPLE 4

Zeolite Beta Synthesis

The moist cake obtained in Example 2 is redispersed an aqueous solution of ammonium acetate (200 g of water and 16 g of ammonium acetate) for the ion exchange. The suspension is heated under agitation for one hour at approximately 80° C.

The suspension is then filtered and the solids thus obtained are re-dispersed in 150 mL demineralized water to be washed. The suspension is then filtered again and a moist zeolite cake in ammonic/alkyl ammonic form is thus obtained again.

An elementary chemical analysis shows the sodium residue in the latter sample to be 112 ppm. The aluminum content is 3.38% ([Al]/[Na]=257).

The product is characterized through X ray diffraction from powders.

EXAMPLE 5

Zeolite Beta Extrusion

A catalyst is prepared based on zeolite beta prepared according to the description in example 4, therefore not subject to calcination, and on alumina in the form of boehmite is. The catalyst has been extruded according to the process described in example 4 EP 847 802.

EXAMPLE 6

Zeolite Beta Synthesis Treated with 5% $(NH_4)_2HPO_4$ 5 g of zeolite beta are loaded into a glass balloon flask, prepared according to example 3, with molar ratio $SiO_2/Al_2O_3=25$, spaciousness index of 19, and 50 ml of a 5% $(NH_4)_2HPO_4$ solution in water.

The suspension is agitated at 90° C. for 1 hour, then the solvent is evaporated under vacuum.

The material thus obtained, in the form of a white powder, is calcined in an stream of air at 550° C. for 5 hours. A calcined material devoid of carbon residue is obtained, the phosphorus content is shown to be 10.14% (11.75% theoretical).

EXAMPLE 7

Zeolite Beta Synthesis Treated with $(NH_4)_2HPO_4$ at 2%

5 g of zeolite beta are loaded into a glass balloon flask, prepared according to example 3, with molar ratio $SiO_2/Al_2O_3=25$, spaciousness index of 19, and 50 ml of a 2% $(NH_4)_2HPO_4$ solution in water.

The suspension is agitated at 90° C. for 1 hour, then the solvent is vacuum evaporated.

The material thus obtained, in the form of a white power, is calcined in an stream of air at 550° C. for 5 hours. A calcined material devoid of carbon residue is obtained, the phosphorus content is found to be 4.59% (4.7% theoretical).

EXAMPLE 8

Zeolite Beta Synthesis Treated with 1% $(NH_4)_2HPO_4$ 5 g of zeolite beta are loaded into a glass balloon flask, prepared according to example 3, with molar ratio $SiO_2/Al_2O_3=25$, spaciousness index of 19, and 50 ml of a 1% $(NH_4)_2HPO_4$ solution in water.

The suspension is agitated at 90° C. for 1 hour, then the solvent is vacuum evaporated.

The material thus obtained, in the form of a white power, is calcined in an stream of air at 550° C. for 5 hours. A calcined material free of carbon residue-is obtained, the phosphorus content is 2.30% (2.35% theoretical).

EXAMPLE 9

Zeolite Beta Synthesis Treated with 4% $H_3BO_3$ 5 g of zeolite beta are loaded into a glass balloon flask, prepared according to example 3, with molar ratio $SiO_2/Al_2O_3=25$, spaciousness index of 19, and 50 ml of a 4% $H_3BO_3$ solution in water.

The suspension is agitated at 90° C. for 1 hour, then the solvent is vacuum evaporated.

The material thus obtained, in the form of a white power, is calcined in an air stream at 550° C. for 5 hours. A calcined material free of carbon residue-is obtained, the boron content is found to be 6.6% (7% theoretical).

EXAMPLE 10

Zeolite Beta Synthesis Treated with $H_3BO_3$ at 2%

5 g of zeolite beta are loaded into a glass balloon flask, prepared according to example 3, with a molar ratio of $SiO_2/Al_2O_3=25$, spaciousness index of 19, and 50 ml of a 2% $H_3BO_3$ solution in water.

This suspension is agitated at 90° C. for 1 hour then the solvent is vacuum evaporated.

The material thus obtained, in the form of a white power, is calcined in an air stream at 550° C. for 5 hours. A calcined material devoid of carbon residue is obtained, with a boron content of 3.5% (3.5% theoretical).

EXAMPLE 11

Extruded Zeolite Beta Synthesis Treated with 2% $(NH_4)_2HPO_4$ 5 g of zeolite beta are loaded into a glass balloon flask, previously extruded with 50% binder (boehmite) prepared according to example 4. Said zeolite, containing as active phase zeolite Beta with molar ratio $SiO_2/Al_2O_3=25$, spaciousness index of 19, is treated with 50 ml of a 2% $(NH_4)_2HPO_4$ solution in water.

The suspension is agitated at 90° C. for 1 hour, then the solvent is vacuum evaporated.

The material thus obtained, in the form of a white power, is calcined in an air stream at 550° C. for 5 hours. A calcined material devoid of carbon residues is obtained, the phosphorus content is found to be 4.79% (4.7% theoretical).

EXAMPLE 12

Extruded Zeolite Beta Synthesis Treated with $H_3BO_3$ at 4%

5 g of previously extruded zeolite beta prepared according to example 4 with 50% binder (boehmite) are loaded into a glass round bottomflask. Said zeolite, containing as active phase zeolite Beta with molar ratio $SiO_2/Al_2O_3=25$, spaciousness index of 19, is treated with 50 ml of a 4% $H_3BO_3$ solution in water.

The suspension is agitated at 90° C. for 1 hour, then the solvent is vacuum evaporated.

The material thus obtained, in the form of a white power, is calcined in an air stream at 550° C. for 5 hours. A calcined material devoid of carbon residues is obtained, with a boron content of 6.8% (7% theoretical).

EXAMPLE 13

Zeolite ZSM-12 Synthesis Treated with 2% $(NH_4)_2HPO_4$ 5 g of zeolite ZSM-12 in acid form, prepared as described in U.S. Pat. No. 3,832,449, with molar ratio $SiO_2/Al_2O_3=102$, spaciousness index 3, and 50 ml of a 2% $(NH_4)_2HPO_4$ solution in water are loaded into a round bottom flask.

The suspension is agitated at 90° C. for 1 hour, then the solvent is vacuum evaporated.

The material thus obtained, in the form of a white power, is calcined in an air stream at 550° C. for 5 hours. A calcined material devoid of carbon residues is obtained, with a boron content of 3.69% (4.7% theoretical).

EXAMPLE 14

Zeolite ZSM-12 Synthesis Treated with $H_3BO_3$ at 2%

5 g of zeolite ZSM-12 in acid form, with molar ratio $SiO_2/Al_2O_3=102$, spaciousness index of 3, and 50 ml of $H_3BO_3$ in a 2% solution in water are loaded into a glass balloon flask.

The suspension is agitated at 90° C. for 1 hour, then the solvent is vacuum evaporated.

The material thus obtained, in the form of a white power, is calcined in an air stream at 550° C. for 5 hours A calcined material devoid of carbon residues is obtained, with a boron content of 3.4% (3.5% theoretical).

EXAMPLE 15 (COMPARATIVE)

Catalytic Test with Untreated Zeolite Beta 4 g of amminal, 10 g of aniline and 125 mg of zeolite beta prepared according to example 3, with molar ratio $SiO_2/Al_2O_3=25$ are loaded in a glass autoclave.

The autoclave is closed and kept under agitation for 6 hours at 150° C.

Finally, the mass is cooled to ambient temperature and the reaction solvent is removed through distillation at reduced pressure.

The reaction product is analyzed by HPLC using the analysis method described in Journal für Praktische Chemie, Band 328, Heft 1, 1986, 142–148.

Conversion: 100%;
selectivity to 4.4'-MDA: 54,99%;
selectivity to 2.4'+2.2'-MDA: 24,67%;
molar ratio 4.4'/(2.4'+2.2'): 2,2
trimers: 11,95%;
heavy components: 10,13%.

EXAMPLE 16

Batch Catalytic Test with Zeolite Beta Treated with $(NH_4)_2HPO_4$ at 5%

4 g of amminal, 10 g of aniline and 1 g of zeolite beta in acid form treated with $(NH_4)_2HPO_4$ at 5%, prepared according to example 6 are loaded in a glass autoclave. The autoclave is closed and kept under agitation for 6 hours at 150° C.

Finally, the mass is cooled to ambient temperature and the reaction solvent is separated through distillation at reduced pressure.

The reaction product is analyzed by HPLC using the analysis method described in Journal für Praktische Chemie, Band 328, Heft 1, 1986, 142–148.
Conversion: 100%;
selectivity to 4.4'-MDA: 69.59
selectivity to 2.4'-MDA: 11.63%;
selectivity to 2.2'-MDA: 0%
molar ratio 4.4'/(2.4'+2.2'): 5.98
trimers and heavy components: 18.76%;

EXAMPLE 17

Batch Catalytic Test with Zeolite Beta Treated with $(NH_4)_2HPO_4$ at 2%

4 g of amminal, 10 g of aniline and 125 mg of zeolite beta in acid form treated with $(NH_4)_2HPO_4$ at 2%, prepared according to example 7 are loaded in a glass autoclave. The autoclave is closed and kept under agitation for 6 hours at 150° C.

Finally, the mass is cooled to ambient temperature and the reaction solvent is separated through distillation at reduced pressure.

The reaction product is analyzed by HPLC using the analysis method described in Journal für Praktische Chemie, Band 328, Heft 1, 1986, 142–148.
Conversion: 100%;
selectivity to 4.4'-MDA: 69.41
selectivity to 2.4'-MDA: 18.70%;
selectivity to 2.2'-MDA: 0%
molar ratio 4.4'/(2.4'+2.2'): 3.71
trimers and heavy components: 11.88%;

EXAMPLE 18

Batch Catalytic Test with Zeolite Beta Treated with $(NH_4)_2HPO_4$ al 1%

4 g of amminal, 10 g of aniline and 125 mg of zeolite beta in acid form treated with $(NH_4)_2HPO_4$ at 1%, prepared according to example 8 are loaded in a glass autoclave. The autoclave is closed and kept under agitation for 6 hours at 150° C.

Finally, the mass is cooled to ambient temperature and the reaction solvent is separated through distillation at reduced pressure.

The reaction product is analyzed by HPLC using the analysis method described in Journal für Praktische Chemie, Band 328, Heft 1, 1986, 142–148.
Conversion: 100%;
selectivity to 4.4'-MDA: 65.60
selectivity to 2.4'-MDA: 20.43%;
selectivity to 2.2'-MDA: 2.61%
molar ratio 4.4'/(2.4'+2.2'): 2.85
trimers and heavy components: 11.36%;

EXAMPLE 19

Catalytic Test in Batch with Extruded Zeolite Beta Treated with $(NH_4)_2HPO_4$ at 2%

4 g of amminal, 10 g of aniline and 125 mg of extruded zeolite beta in acid form treated with $(NH_4)_2HPO_4$ at 2%, prepared according to example 11 are loaded in a glass autoclave. The autoclave is closed and kept under agitation for 6 hours at 150° C.

Finally, the mass is cooled to ambient temperature and the reaction solvent is separated through distillation at reduced pressure.

The reaction product is analyzed by HPLC using the analysis method described in Journal für Praktische Chemie, Band 328, Heft 1, 1986, 142–148.
Conversion: 100%;
selectivity to 4.4'-MDA: 69.1%
selectivity to 2.4'-MDA: 21.19%;
selectivity to 2.2'-MDA: 4.36%
molar ratio 4.4'/(2.4'+2.2'): 2.70
trimers and heavy components: 5.34%;

EXAMPLE 20

Batch Catalytic Test with Zeolite Beta Treated with $H_3BO_3$ al 4%

4 g of amminal, 10 g of aniline and 1 g of zeolite beta in acid form treated with $H_3BO_3$ at 4%, prepared according to example 9, are loaded in a glass autoclave. The autoclave is closed and kept under agitation for 6 hours at 150° C.

Finally, the mass is cooled to ambient temperature and the reaction solvent is separated through distillation at reduced pressure.

The reaction product is analyzed by HPLC using the analysis method described in Journal für Praktische Chemie, Band 328, Heft 1, 1986, 142–148.
Conversion: 100%;
selectivity to 4.4'-MDA: 67.57
selectivity to 2.4'-MDA: 9.73%;
selectivity to 2.2'-MDA: 0%
molar ratio 4.4'/(2.4'+2.2'): 6.94
trimers and heavy components: 22.68%;

EXAMPLE 21

Batch Catalytic Test with Zeolite Beta Treated with $H_3BO_3$ at 2%

4 g of amminal, 10 g of aniline and 125 mg of zeolite beta in acid form treated with $H_3BO_3$ at 2% are loaded in a glass autoclave, as shown in example 10. The autoclave is closed and kept under agitation for 6 hours at 150° C.

Finally, the mass is cooled to ambient temperature and the reaction solvent is separated through distillation at reduced pressure.

The reaction product is analyzed by HPLC using the analysis method described in Journal für Praktische Chemie, Band 328, Heft 1, 1986, 142–148.
Conversion: 100%;
selectivity to 4.4'-MDA: 73.04
selectivity to 2.4'-MDA: 14.54%;
selectivity to 2.2'-MDA: 0%
molar ratio 4.4'/(2.4'+2.2'): 5.02
trimers and heavy components: 12.41%;

EXAMPLE 22

Batch Catalytic Test with Extruded Zeolite Beta Treated with $H_3BO_3$ al 4%

4 g of amminal, 10 g of aniline and 1 g of extruded zeolite beta in acid form treated with $H_3BO_3$ at 4% are loaded in a glass autoclave, as in example 12. The autoclave is closed and kept under agitation for 6 hours at 150°.

Finally, the mass is cooled to ambient temperature and the reaction solvent is separated through distillation at reduced pressure.

The reaction product is analyzed by HPLC using the analysis method described in Journal für Praktische Chemie, Band 328, Heft 1, 1986, 142–148.
Conversion: 100%;
selectivity to 4.4'-MDA: 67.59%
selectivity to 2.4'-MDA: 15.49%;
selectivity to 2.2'-MDA: 3.21%
molar ratio 4.4'/(2.4'+2.2'): 3.63
trimers and heavy components: 13.7%;

EXAMPLE 23 (COMPARATIVE)

Catalytic Test with Untreated ZSM-12 Zeolite 4 g of amminal, 10 g of aniline and 1 g of extruded ZSM 12 zeolite in acid form with molar ratio $SiO_2/Al_2O_3$=102 are loaded in a glass autoclave.

The autoclave is closed and kept under agitation for 6 hours at 150° C. Finally, the mass is cooled to ambient temperature and the reaction solvent is separated through distillation at reduced pressure.

The reaction product is analyzed by HPLC using the analysis method described in Journal für Praktische Chemie, Band 328, Heft 1, 1986, 142–148.
Conversion: 100%;
selectivity to 4.4'-MDA: 54.50%;
selectivity to 2.4'+2.2'-MDA: 30.36%
molar ratio 4.4'/(2.4'+2.2'): 1.66
trimers: 10.76%;
heavy components: 2.87%.

EXAMPLE 24

Catalytic Test with ZSM 12 Treated with $(NH_4)_2HPO_4$ at 2%

4 g of amminal, 10 g of aniline and 19 of ZSM 12 zeolite in acid form treated with $(NH_4)_2HPO_4$ at 2%, as in example 13 are loaded in a glass autoclave.

The autoclave is closed and kept under agitation for 6 hours at 150° C.

Finally, the mass is cooled to ambient temperature and the reaction solvent is separated through distillation at reduced pressure.

The reaction product is analyzed by HPLC using the analysis method described in Journal für Praktische Chemie, Band 328, Heft 1, 1986,142–148.
Conversion: 100%;
selectivity to 4.4'-MDA: 64.86%
selectivity to 2.4'-MDA: 11.85%;
selectivity to 2.2'-MDA: 0.%
molar ratio 4.4'/(2.4'+2.2'): 5.47
trimers and heavy components: 23.29%;

EXAMPLE 25

Catalytic Test with ZSM 12 Treated with $H_3BO_3$ at 2%

4 g of amminal, 10 g of aniline and 1 g of zeolite ZSM 12 in acid form treated with $H_3BO_3$ at 2% are loaded in a glass autoclave, as shown in example 14. The autoclave is closed and kept under agitation for 6 hours at 150° C.

Finally, the mass is cooled to ambient temperature and the reaction solvent is separated through distillation at reduced pressure.

The reaction product is analyzed by HPLC using the analysis method described in Journal für Praktische Chemie, Band 328, Heft 1, 1986, 142–148.
Conversion: 100%;
selectivity to 4.4'-MDA: 66.40%
selectivity to 2.4'-MDA: 11.20%;
selectivity to 2.2'-MDA: 2.95%
molar ratio 4.4'/(2.4'+2.2'): 4.69
trimers and heavy components: 19.62.%;

EXAMPLE 26

Catalytic Test in a Fixed Bed Reactor with Untreated Zeolite Beta (Comparative)

5 cm$^3$ of zeolite beta prepared according to example N. 3, with molar ratio $SiO_2/Al_2O_3$=25, compressed at 20 ton and sifted at 70–100 mesh are loaded in a tubular reactor with a diameter of 12.5 mm and length of 390 mm. A mixture of 30% amminal by volume in aniline, is then fed into the reactor at a temperature of 180° C., at 4 bar pressure and an L.H.S.V. (Liquid Hourly Space Velocity) of 7.2 h$^{-1}$, referred to the active phase.

Samples are taken at the times indicated in table 1 which, following solvent separation at reduced pressure, are analyzed according to the previously described method.

For all samples the amminal conversion is total.

TABLE 1

| Time on stream (t.on.s.) (h) | Ratio 4.4'/(2.4' + 2.2') | 4.4' MDA % | 2.4' + 2.2' MDA % | Heavy components + Trimers % |
|---|---|---|---|---|
| 2 | 2.06 | 63.40 | 30.79 | 5.81 |
| 4 | 2.13 | 64.04 | 30.06 | 5.36 |
| 6 | 2.08 | 63.77 | 30.56 | 5.67 |
| 20 | 2.08 | 64.01 | 30.72 | 5.27 |
| 24 | 2.14 | 64.31 | 30.07 | 5.62 |

EXAMPLE 27

Catalytic Test in Fixed Bed Reactor with Zeolite Beta Treated with $(NH_4)_2HPO_4$ at 1%

5 cm$^3$ of zeolite beta, treated with $(NH_4)_2HPO_4$ at 1% (prepared according to example 8), compressed at 20 ton and sifted with 70–100 mesh are loaded in a tubular reactor with a diameter of 12,5 mm and length 390 mm. A mixture of 30% amminal by volume in aniline is then fed into the reactor, at a temperature of 180° C., at 4 bar pressure and an L.H.S.V. (Liquid Hourly Space Velocity) of 7.2 h$^{-1}$, referred to the active phase.

Samples are taken at the times indicated in table 2 which, following solvent separation at reduced pressure, are analyzed according to the previously described method.

For all samples amminal conversion is total.

TABLE 2

| t.on.s. (h) | Ratio 4.4'/(2.4' + 2.2') | 4.4' MDA % | 2.4' + 2.2' MDA % | Heavy components + Trimers % |
|---|---|---|---|---|
| 2  | 2.48 | 66.72 | 26.83 | 6.45  |
| 4  | 2.52 | 65.26 | 25.9  | 8.84  |
| 18 | 2.53 | 63.49 | 25.09 | 11.42 |
| 20 | 2.54 | 62.79 | 24.72 | 12.49 |
| 22 | 2.52 | 62.04 | 24.6  | 13.33 |
| 24 | 2.60 | 60.35 | 23.2  | 16.44 |

What is claimed is:

1. A process for the preparation of methane diphenyl diamine or a mixture of methane diphenyl diamine and its higher homologues having the general formula (I):

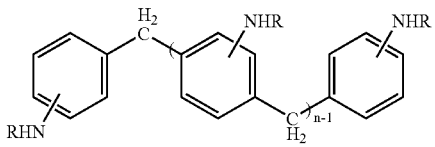

where R is independently selected from hydrogen, a C1 to C8 alkyl group, a C4 to C10 cycloalkyl group or a C6 to C12 aromatic group and n is a whole number from 1 to 5 so as to give a functionality from 2 and 6, which comprises carrying out the re-arrangement reaction of the intermediate having general formula (II):

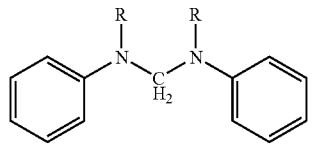

in the presence of a zeolite in acid form with a "spaciousness index" from 2.5 to 19 modified on the surface by a process comprising i) one or more treatments with an aqueous solution comprising phosphoric acid and/or boric acid, as is, and, optionally, comprising a salt thereof, ii) removal of at least part of the solvent and iii) calcining the treated catalyst.

2. A process according to claim 1, in which the zeolite comprises a synthetic crystalline material having the composition (III):

$$M^{n+}{}_{x/n}[(AlO_2)^-{}_x(SiO_2)]\cdot(H_2O)_p \qquad [III]$$

where x is less than 1, p is a whole number greater than or equal to 1, M is a metal from Groups IA or IIA, or is a lanthanide, n is the valency of M, and where M may be partially or totally exchanged for $H^+$, $(NH4)^+$, or for $(NR'4)^+$ where R' is an alkyl group or an aryl group. aliphatic hydrocarbons, optionally substituted aromatic hydrocarbons, halogenated aromatic hydrocarbons and aniline.

3. A process according to claim 2, in which the zeolite is selected from beta zeolite, mordenite, ZSM-12, MCM-22 and ERB-1.

4. A process according to claim 3, in which the zeolite is selected from beta zeolite and ZSM-12.

5. A process according to claim 1 in which the surface modification treatment is carried out by submerging zeolite solid particles in a liquid phase comprising phosphoric acid and/or boric acid, as is and, optionally, comprising a salt thereof, diluted in water at a concentration of 0.1 and 10% by weight and at a temperature ranging between 20 and 100° C.

6. A process according to claim 1 in which, at the end of the treatment in step i) to modify the zeolite, at least part of the liquid phase is removed and the remaining solids are calcined a temperature of at least 400° C.

7. A process according to claim 1 in which the surface modification treatment is repeated one or more times.

8. A process according to claim 1 in which the zeolite is modified as is or after the partial isomorphic substitution of aluminium by a metal selected from boron, iron and gallium.

9. A process according to claim 1 in which the surface-modified zeolite is in the form of extruded tablets and the modification is performed directly on the extruded tablets.

10. A process according to claim 1 in which the zeolite is mixed with a binder.

11. A process according to claim 1 in which the rearrangement reaction is carried out at a temperature of 50 to 250° C.

12. A process according to claim 1 in which the rearrangement reaction takes place in the presence of a solvent, selected from optionally substituted aliphatic hydrocarbons, optionally substituted aromatic hydrocarbons, halogenated aromatic hydrocarbons and aniline.

13. A process according to claim 12, in which the solvent is selected from aniline and a chlorinated aromatic solvent.

14. A process according to claim 1 in which the intermediate contains water in a quantity equal to or less than 3% by weight.

15. A process for the preparation of methane diphenyl diamine of general formula (I),

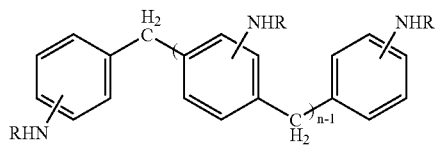

where R is independently selected from hydrogen, a C1 to C8 alkyl group, a C4 to C10 cycloalkyl group and a C6 to C12 aromatic group and n is a whole number from 1 to 5 so as to give a functionality from 2 and 6, in which a rearrangement reaction is carried out by contacting a zeolite in acid form with a "spaciousness index" from 2.5 to 19 modified on the surface by a process comprising i) one or more treatments with an aqueous solution comprising phosphoric acid and/or boric acid, as is, and, optionally, comprising a salt thereof, ii) removal of at least part of the solvent and iii) calcining the treated catalyst, with a reaction mixture comprising aniline, or a derivative of aniline, and formaldehyde, or a compound capable of producing formaldehyde under the reaction conditions.

16. A process according to claim 15, in which the reaction is carried out with an excess of aniline, or its derivative, which acts as a reagent and a solvent.

17. A process for the production of a compound having general formula (I)

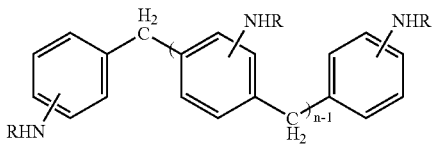

wherein R is independently selected from hydrogen, a C1 to C8 alkyl group, a C4 to C1 cycloalkyl group and a C6 to C12 aromatic group and n is a whole number from 1 to 5 so as to give a functionality from 2 and 6, comprising:
  (a) reacting aniline, or a derivative of aniline, and formaldehyde, or a precursor of formaldehyde, so as to form an amine, optionally in the presence of a solvent;
  (b) removing water if present, from the reaction product of (a) to a residual concentration of water of 3% or less by weight of the amine;
  (c) optionally diluting the product of step (b) in a solvent;
  (d) isomerising the amine by feeding it into a reaction zone containing a zeolite in acid form with a "spaciousness index" of 2.5 to 19, modified on the surface by a process comprising i) one or more treatments with an aqueous solution comprising phosphoric acid and/or boric acid, as is, and, optionally, comprising a salt thereof, ii) removal of at least part of the solvent and iii) calcining the treated catalyst, and wherein the reaction zone in step d) is at an ambient pressure or such as to maintain the reagent mixture in a liquid state at a temperature of 50 to 250° C.; and
  (e) recovering the methane diphenyl diamine, and/or its higher homologues.

18. A process according to claim 17, in which the amine (II) is fed to the reaction zone in a discontinuous manner using a vertical reactor fitted with two or more lateral inlets.

19. A process according to claim 17 in which the mixture obtained after isomerisation is totally or partially recycled in step a) or in step d).

20. A process for the production of a compound having general formula (I)

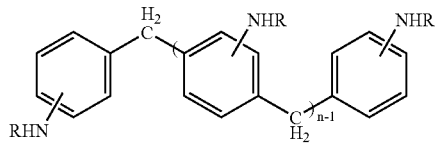

where R is independently selected from hydrogen, a C1 to C8 alkyl group, a C4 to C10 cycloalkyl group and a C6 to C12 aromatic group and n is a whole number greater than, or equal to one, suitably from 1 to 5 so as to give a functionality from 2 and 6,
  which comprises reacting aniline, or one of its derivatives, and formaldehyde, or one of its precursors, in a single reaction step in the presence of a zeolite in acid form with a "spaciousness index" of 2.5 to 19 modified on the surface by a process comprising i) one or more treatments with an aqueous solution comprising phosphoric acid and/or boric acid, as is, and, optionally, comprising a salt thereof, ii) removal of at least part of the solvent and iii) calcining the treated catalyst.

21. A process according to claim 20, in which the aniline/formaldehyde molar ratio is from 2 to 15, the reaction temperature is from 50 to 250° C. and the pressure is such that the water added with the reagents, or formed during the reaction, is continuously removed from the reaction step.

22. A process according to claim 20 in which times in the liquid phase range between 0.5 and 10 hours and the catalyst/load weight ratio ranges between 1/20 and 1/300.

* * * * *